(12) United States Patent
Samson et al.

(10) Patent No.: US 9,691,176 B2
(45) Date of Patent: Jun. 27, 2017

(54) METHOD AND SYSTEM FOR FORMING A VIRTUAL MODEL OF A HUMAN SUBJECT

(71) Applicant: TECHMED 3D INC., Lévis (CA)

(72) Inventors: Jean-Pierre Samson, Lévis (CA); Michel Babin, St-Nicolas (CA)

(73) Assignee: Techmed 3D Inc., Lévis (CA)

( * ) Notice: Subject to any disclaimer, the term of this patent is extended or adjusted under 35 U.S.C. 154(b) by 272 days.

(21) Appl. No.: 14/359,056

(22) PCT Filed: Nov. 16, 2012

(86) PCT No.: PCT/CA2012/001059
§ 371 (c)(1),
(2) Date: May 16, 2014

(87) PCT Pub. No.: WO2013/071416
PCT Pub. Date: May 23, 2013

(65) Prior Publication Data
US 2014/0375629 A1 Dec. 25, 2014

Related U.S. Application Data

(60) Provisional application No. 61/561,057, filed on Nov. 17, 2011.

(51) Int. Cl.
*G06T 17/00* (2006.01)
*A41H 1/02* (2006.01)
(Continued)

(52) U.S. Cl.
CPC ............. *G06T 17/00* (2013.01); *A41H 1/02* (2013.01); *A43D 1/025* (2013.01); *A61B 5/1075* (2013.01);
(Continued)

(58) Field of Classification Search
None
See application file for complete search history.

(56) References Cited

U.S. PATENT DOCUMENTS 5,712,803 A 1/1998 Garuet-Lempirou
5,886,775 A * 3/1999 Houser .............. G01S 5/0247
356/4.01
(Continued)

FOREIGN PATENT DOCUMENTS

EP 0750175 12/1996
WO WO2004113831 12/2004
(Continued)

OTHER PUBLICATIONS

Canadian Patent Office International Search Report dated Feb. 25, 2013, International Application No. PCT/CA2012/001059 (2 pages).

*Primary Examiner* — Andrew G Yang
(74) *Attorney, Agent, or Firm* — McCracken & Gillen LLC (57) ABSTRACT

The method uses a hand-held scanner and a scanning module and can include: providing module reference data concerning the scanning module; immobilizing the subject relative to the scanning module; obtaining a plurality of depth images of the immobilized subject and module, the depth images being from corresponding different points of view relative to a ground reference; determining a position and an orientation of the scanning module in each one of the depth images using the module reference data; and forming the virtual model of the subject, including registering the plurality of depth images using the determined position and orientation of the scanning module.

21 Claims, 6 Drawing Sheets

(51) Int. Cl.
*A43D 1/02* (2006.01)
*A61B 5/107* (2006.01)
*G06T 15/00* (2011.01)
*A61B 5/00* (2006.01)

(52) U.S. Cl.
CPC ........ G06T 15/005 (2013.01); *A43D 2200/60* (2013.01); *A61B 5/0077* (2013.01); *G06T 2215/16* (2013.01)

(56) References Cited

U.S. PATENT DOCUMENTS

| | | | |
|---|---|---|---|
| 6,262,738 B1 * | 7/2001 | Gibson | G06T 15/06 345/419 |
| 7,256,899 B1 | 8/2007 | Faul et al. | |
| 8,773,508 B2 | 7/2014 | Daniel et al. | |
| 2003/0033207 A1 | 2/2003 | Litke et al. | |
| 2006/0140463 A1 * | 6/2006 | Rutschmann | A61B 5/0064 382/128 |
| 2007/0253004 A1 | 11/2007 | Danenberg et al. | |
| 2009/0067706 A1 | 3/2009 | Lapa | |
| 2010/0134598 A1 | 6/2010 | St-Pierre et al. | |
| 2010/0262054 A1 | 10/2010 | Summit et al. | |
| 2011/0074930 A1 | 3/2011 | Hérbert et al. | |

FOREIGN PATENT DOCUMENTS

| | | |
|---|---|---|
| WO | WO2008070537 | 6/2008 |
| WO | WO2011138741 | 11/2011 |

\* cited by examiner

METHOD AND SYSTEM FOR FORMING A VIRTUAL MODEL OF A HUMAN SUBJECT

FIELD

The improvements generally relate to the field of 3D scanning of live subjects with a hand-held scanner, and can more particularly apply to the scanning of portions of the human body.

BACKGROUND 3D scanning is well known per se. Non-contact, hand-held scanners are available on the market and can be used to obtain a 3D representation of an immobile object by moving the hand-held scanner around the object, that is relative to a reference located at a fixed position on the ground (ground reference), while maintaining the field of view of the scanner oriented toward the object. Non-contact scanning can be done either actively or passively. Active scanning involves emitting a light signal or the like which is reflected on the surface to be scanned, whereas passive scanning does not control emission and can rather involve a process similar to detecting depth using human binocular vision. Hand-held scanners are typically surface scanners. Surface scanning is different from solid scanning in the sense that in surface scanning only information about the surface of the scanning subject is obtained, to form a shell model of the object, whereas in solid scanning, information about the subject (typically density), is obtained at various depths across it, such as in X-ray computed tomography for instance (CT).

With a hand-held scanner, for most situations, a single scan taken from a single position and orientation of the scanner in space will not produce a complete model of the subject. Multiple scans, even hundreds, from many different directions are usually required to obtain information about all sides of the subject. These scans each produce a depth image which have to be brought in a common reference system, a process that will be referred to herein as registration, to create a complete model inclusive of hidden faces in individual ones of the depth images. The depth images typically include at least a depth value for each pixel corresponding to the field of view of the scanner, so the depth images can be 3D images if the scanner has a 2D array of pixels.

Although known hand-held scanner based scanning systems and methods were satisfactory to a certain degree, there remained room for improvement. In particular, there remained applications where the step of registration met difficulties. One example lies in instances where the scanning system "lost" the common reference system and then became unable to register later images with earlier images. This is a particular challenge when dealing with live subjects which can move or change its shape during scanning.

SUMMARY

It was found that at least in some human subject applications, precision and/or reliability can be improved by using an independent scanning module which is to be scanned together with the subject. Software can recognize the position and orientation of the scanning module in the images, and a common reference system can established for the subject based on the scanning module recognition. In this manner, the plurality of images of the subject can be registered in accordance with the scanning module-based common reference system.

Henceforth, in accordance with one aspect, there is provided a method of forming a virtual model of a subject using at least a hand-held scanner and a scanning module, the method comprising: providing module reference data concerning the scanning module; immobilizing the subject relatively to the scanning module; using the hand-held scanner to obtain a plurality of depth images of the immobilized subject and module, the depth images being taken at different positions of the hand-held scanner relative to a ground reference; for each one of the plurality of depth images, determining a position and an orientation of the scanning module in the depth image using the module reference data, and establishing a common reference system for the subject using the determined position and orientation of the scanning module; forming the virtual model of the subject, including registering the plurality of depth images in the common reference system associated to the scanning module.

In accordance with another aspect, there is provided a method of forming a virtual model of a subject using at least a hand-held scanner and a scanning module, the method comprising: providing module reference data concerning the scanning module; immobilizing the subject relative to the scanning module; obtaining a plurality of depth images of the immobilized subject and module, the depth images being from corresponding different points of view relative to a ground reference; determining a position and an orientation of the scanning module in each one of the depth images using the module reference data; forming a virtual model of the subject, including registering the plurality of depth images using the determined position and orientation of the scanning module.

In accordance with another aspect, there is provided a system for forming a virtual model of a subject, the system comprising: a scanning module adapted to a type of the subject, for the subject to be immobilizable in abutment with the scanning module; a hand-held scanner to obtain a plurality of depth images of the immobilized subject and module, the depth images being taken at different positions of the hand-held scanner relative to a ground reference; module reference data concerning the scanning module; a software for determining a position and an orientation of the scanning module in each of the depth images using the module reference data, establishing a common reference system for the subject using the determined position and orientation of the scanning module; wherein the virtual model of the subject can be formed including registering the plurality of depth images in the common reference system associated to the scanning module.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
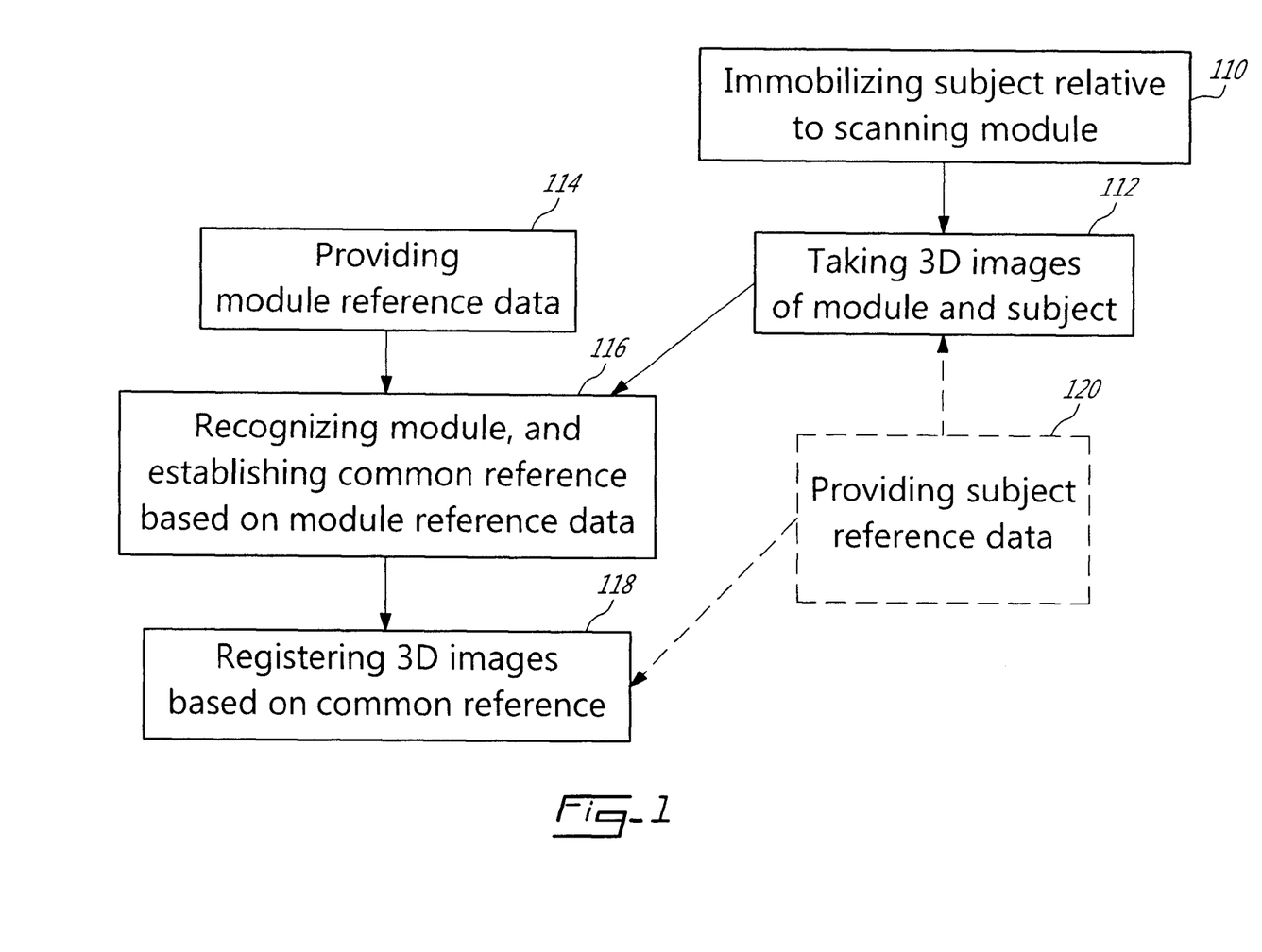
FIG. 1 is a flow chart of an example method for forming a virtual model of a subject.

Referring to FIG. 1, an example method includes immobilizing the subject to be scanned relative to a scanning module 110. The configuration of the scanning module will depend on the type of subject being scanned. Several examples of subject types and scanning modules are detailed below. Depth images of the combined subject and scanning module are then taken with a hand-held scanner 112, which will be referred to herein as scanning. The depth images typically include at least a depth value for each pixel corresponding to the field of view of the scanner, so the depth images are typically 3D images if the scanner has a 2D array of pixels. The depth images can optionally include further information for each pixel, such as color, brightness, etc. Typically, each one of the depth images only shows a portion of the subject and scanning module which is in the field of view of the hand-held scanner, so the hand-held scanner is moved relative to a ground reference in order to have depth images showing all sides of the subject which are desired to be included in the 3D model. Once these depth images are made available, they all typically include information on exposed surfaces of the subject and of the module. To form the model, the information about the different surfaces they include needs to be registered together in a common reference. In this example, the common reference is established with respect to the scanning module. More particularly, module reference data concerning the specific scanning module used can be made available 114. As will be detailed below, this can be achieved by scanning the scanning module alone beforehand, or alternately, by providing a satisfactory virtual model of the scanning module by other suitable means. A software can then recognize the position and orientation of the scanning module in the depth images and establish the common reference plane with respect to the scanning module 116. The same software, or another, can then be used to do the registration based on this common reference plane 118. Additional software work can then be done on the registered model to cure holes, correct triangulation errors, remove noise, etc. if desired, which can be done using subject reference data 120. Positioning features such as adhesive scanning targets can optionally be applied at specific physiological areas on the subject prior to scanning to later serve as additional subject reference data points if desired.

Figure 2:
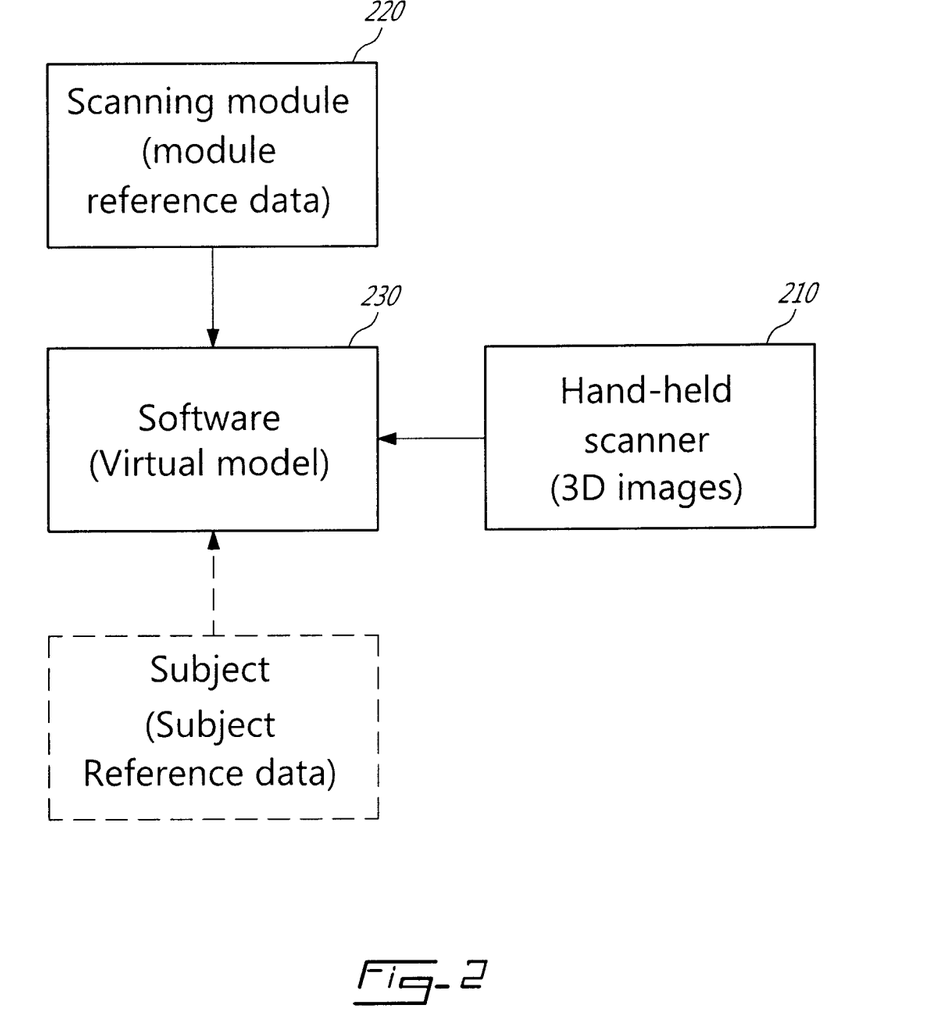
FIG. 2 is block diagram of an example system for forming a virtual model of a subject.

FIG. 2 is a block diagram showing an example system to realize the method shown in FIG. 1. In this example, the system includes three main components: a hand-held scanner 210, a scanning module 220 and a software 230. The software 230 can be incorporated in a separate computer, for instance, or be incorporated in the hand-held scanner itself. The subject will be immobilized relative to the scanning module 220 with which it will be scanned by the hand-held scanner 210 and analysed by the software 230. Module reference data concerning the scanning module is provided to the software for the software 230 to be able to recognize the scanning module in the depth images from the hand-held scanner 210. Any satisfactory hand-held scanner 210 that outputs a triangulated representation of the subject can be used. The scanning module 220 can be adapted according to the basic technology for data acquisition and 3D positioning of the hand-held scanner selected.

The scanning module 220 can be said to have 3 main purposes: immobilization and stability of the subject (relative to the scanning module that is), making it possible to record a complete scan of the subject from all desired angles, and pre-align the subject. It's the pre-alignment functionality that is the key to the automation done by the software 230. It may be possible to pre-align the subject using the scanning module regardless of the hand-held scanner used, but the strategy behind it may be slightly different from one technology to another. An example of a hand-held scanner which can be used is the ErgoSCAN™ scanner manufactured by Creaform Inc. This type of scanner can recognize rounded positioning targets of 5 mm that can be affixed to the scanning module in the field of view of the hand-held scanner. The observed pattern of those targets can be analysed by the scanner to determine the relative position and orientation of the hand-held scanner relative to the scanning module. The pattern of targets can be pre-recorded to constitute module reference data.

In an other embodiment, the shape and size of the scanning module itself may provide sufficient distinctive features for its relative position and orientation to be detectable by software based on the depth images taken without requiring the use of scanning targets.

In still an other embodiment, it is possible to use an electromagnetic field emitter housed in the scanning module and of which the exact disposition of the emitted electromagnetic field in the vicinity of the scanning module is known. Then, by using an electromagnetic field detector in the hand-held scanner, the relative position and orientation of the hand-held scanner relative to the scanning module can be determined for each of the depth images taken, and the common reference system established. In this case, the configuration of the electromagnetic field is made part of the module reference data which software can access to establish the common reference system.

Software can: pre-configure scanning parameters as a function of the type of subject, automatically perform post-treatment operations on the model, and detect features on the subject to correct its alignment and calculate a set of pre-defined measurements, for instance.

One step of the scanning process can consist in identifying the type of object, which can be said to provide subject reference data. The subject reference data can either be predefined in the software, or can be inputted via a user interface, for instance. In one embodiment, the subject reference data can be used to pre-configure the hand-held scanner to record that type of subject, which can include settings like resolution, laser power, camera shutter time, scanning volume size and location. Subject reference data can also include information on the basic geometry of the subject. Also, scanning targets can be used on particular physiological features of the subject to assist in later registration, alignment correction, or completion of the virtual model, in which case the subject reference data can include a definition of the location of such scanning targets.

For instance, if the pre-alignment of the subject relative to the scanning module is imperfect, the software can be used to recognize features of the known subject type using the subject reference data and can correct the alignment of the subject in a same way every time according to the subject's own features. Alternately, when comparing virtual images of the same object type, the subject reference data can assist in the relative alignment of the virtual images. With the subject aligned, it is possible to calculate a set of pre-defined measurements. Those measurements can be defined according to the subject type and in the context of the application in which the model is to be used.

Having discussed the method and system generally, different specific application examples will now be detailed.

Figure 3A:
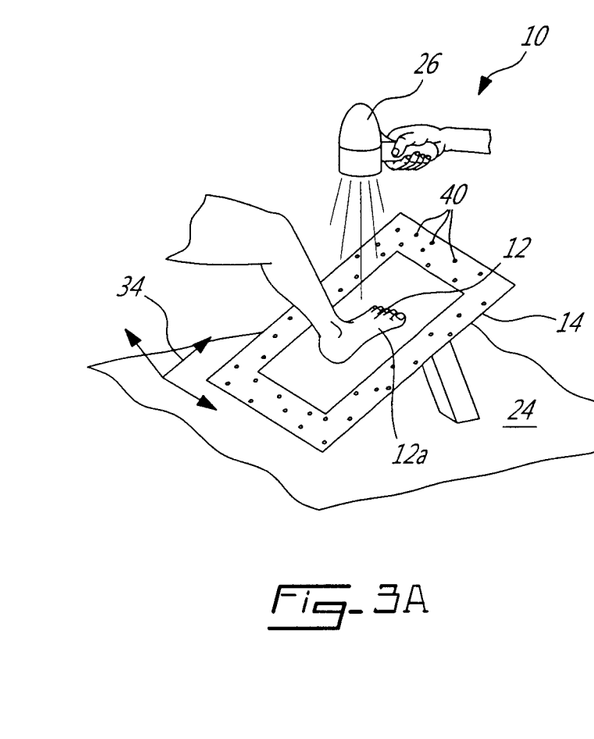
FIGS. 3A to 3C illustrate the forming of a virtual model of a human foot.

FIG. 3A shows a first embodiment of a system 10 where the subject 12 is a human foot. For this type of subject, an example of a scanning module 14 (better seen at FIG. 3B) can include a solid frame 16 with a central aperture which houses a foot-receiving transparent pane 20. This allows to immobilize the foot relative to the scanning module while simultaneously allowing scanning of the underside of the foot. In this particular example the scanning module 14 has two removable legs which receive the solid frame 16 and transparent pane 20 associate thereto at a convenient sloping angle with respect to the ground 24, for the foot placed thereon to be relatively comfortable in remaining immobile during the scanning process.

Referring back to FIG. 3A, the human foot subject 12 is shown placed in stable abutment against the foot-receiving transparent pane and is kept immobilized relative to the scanning module throughout the scanning process. The scanning process includes taking a plurality of depth images of the combined foot 12 and scanning module 14 with the hand-held scanner 26. The depth images are taken from different locations and orientations as the hand-held scanner is moved manually by the hand of an operator relative to the ground 24. The hand-held scanner 26 is moved relative to a ground reference in a manner that depth images are obtained showing each portion of the exposed surface of the foot. The hand-held scanner 26 is also moved to the side of the scanning module opposite the leg to take depth images of the underside of the foot 12 across the transparent pane 20 of the scanning module 14. Because the hand-held scanner 26 is a surface scanner in this example, each depth image only includes information about the exposed surface of the subject which faces the hand-held scanner (i.e. that is exposed to the field of view of the hand-held scanner), and does not include information concerning the surface of the subject which faces away from the hand-held scanner 26.

Figure 3B:
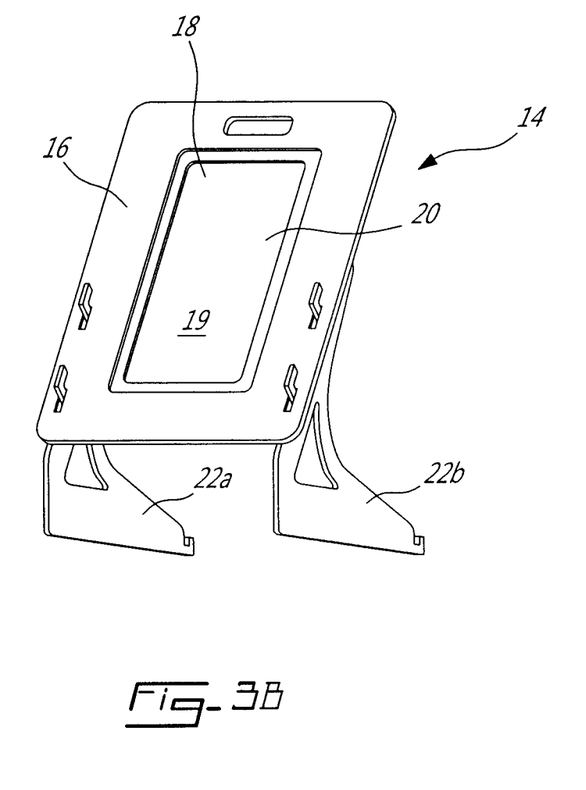
Figure 3C:
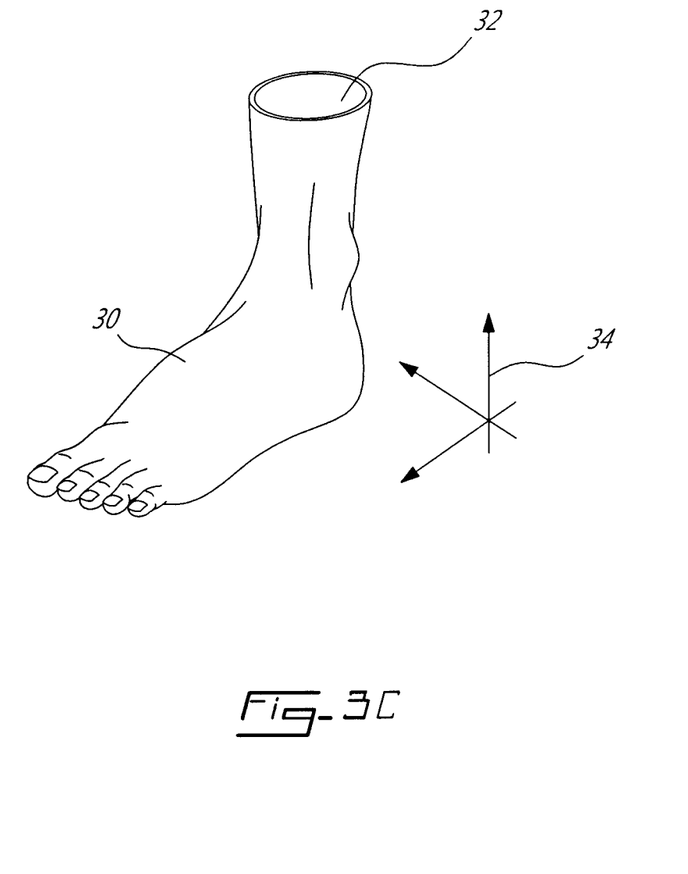

Each of the depth images typically includes information concerning the distance of a first obstacle in the path of light for each pixel in a field of view of the hand-held scanner 26. To form a virtual model of the subject, an example 30 of which is shown in FIG. 3C, the information available in the different depth images needs to be registered in a common reference system. It will be noted here that the virtual model which is formed in this example is of a 3D shell type, i.e. it is a hollow shell model of the foot which combines the shape information of the external surface of the foot from the different depth images but which does not have information from the inside of the foot, such as bones or the like. Henceforth, it can be expected that the shell model be left with a hole 32 in the shin which corresponds to scan limit.

In this method, the common reference system 34 is established in relation to the scanning module 14, relative to which the subject 12 is immobilized during the scanning.

More particularly, module reference data is obtained prior to registration. The module reference data is of a nature such that the position and orientation of the hand-held scanner 26 relative to the scanning module 14 can be determined for each of the depth images. Since the subject is immobilized relative to the scanning module, the relative position and orientation with the subject also becomes known. Henceforth, establishing a common reference system 34 in relation to the scanning module corresponds to establishing a common reference system 34 in relation to the subject. For example, if Cartesian coordinates are used, an origin of the common reference system 34 for the subject can be positioned at a fixed location relative to the scanning module 14, and the axes can be oriented in predetermined orientations relative to the scanning module 14.

In this specific embodiment of a foot subject type, the X and Y axes can be oriented to correspond to a plane coinciding with the foot abutment surface 19 of the transparent pane 20, and the normal Z axis correspond to the height, for instance.

There are several ways by which the module reference data can establish the common reference system in relation with the scanning module.

In a first embodiment using an ErgoSCAN™ hand-held scanner, the common reference system can be achieved using a plurality of reflective targets 40 on the scanning module. For instance, circular reflective targets having a 5 mm diameter with an adhesive backing can be applied by hand on the scanning module. If they are hand-applied, the reflective targets will be spaced from one another with a certain degree of randomness and so any combination of three or more of the scanning targets being detected in the field of view of the hand-held scanner will correspond to a unique combination of scanning target disposition allowing identify the position and orientation of the common reference system.

Henceforth, the scanning module can be scanned alone, to create a virtual model thereof in which its exact signature of scanning target disposition is included, and can include the common reference system (origin and axis orientation). This virtual model can form the module reference data. Henceforth, when the scanner is used to take depth images of the scanning module and of the subject which is immobilized thereon, as long as sufficient scanning targets are within the field of view, software can access the virtual model, compare the detected scanning targets to the ones in the virtual model, and automatically determine the position and orientation of the scanning module with respect to the position and orientation of the hand-held scanner.

This can be particularly helpful in cases of a discontinuity between scanning portions of the subject.

For example, in a typical scanning of a human foot in accordance with the prior art, the images were registered by recognizing surfaces of the subject in individual 3D images and associating the images in a relative position and orientation in a manner to match the recognized common surfaces. However, passing the hand-held scanner from the exposed upper portion of the foot to the exposed under portion of the foot was particularly tricky due to the size of the exposed surface on the side of the foot, and often led to the inability of the software to register images of the underside of the foot with images of the upper side of the foot.

Using the scanning module, the images of the underside of the foot and the images of the upper side of the foot can both be independently referenced using the common reference which is based on the scanning module, and therefore be registered based on the common reference even if the event of a break in the images as the hand-held scanner passes on the side of the scanning module. The images taken from the under portion of the foot can thus be merged with the images taken from the upper portion of the foot in the common reference plane as long as the foot did not move relative to the scanning module between both sets of images.

Further to the use of module reference data, subject reference data can also be obtained prior to registration. The subject reference data can include information concerning a rough expected shape, position and orientation of the subject in relation to the scanning module which can help in creating the model of the subject. For instance, once the scan has been completed, a rough representation of the pre-aligned object on the scanning module can be obtained. This representation can be far from perfect and need post-treatment operations as it may contain holes, noise and/or triangulation errors. By knowing the subject type and its global orientation in space, it also becomes possible to automatically fill the holes, clean-up the noise and correct triangulation errors by using 3D post-treatment algorithms.

Subject reference data can also include information pertaining to positioning features used on the subject. For example, positioning features such as scanning targets can be affixed on the subject at key locations which can correspond to specific anatomical features. In the case of a foot, scanning targets can be positioned on the lateral and medial malleolus for instance. Such positioning features can help the software identifying those points for alignment and comparison applications (i.e. monitoring the evolution of the subject foot in time, or using the scan of the subject foot in relation to a shoe, boot, orthotic foot brace, or the like).

In the illustrated embodiment, the foot is simply abutted against the transparent pane, henceforth, a plane corresponding to the underside of the foot is determined in space relative to the common reference system 34, but the foot itself is free to be pivoted to a certain degree about the Z axis. In certain cases, it can be advantageous for post-treatment that the features of the foot have a specific alignment with the X or Y axis. This can be achieved to some extent by using additional abutment means on the scanning module to physically lock the pivoting of the foot relative to predetermined features (e.g. a protruding transparent wall abutment or the like, not illustrated), or it can be done virtually by a software. If using a software, subject reference data such as the type and general geometry considerations of the subject, or predefined position of subject scanning targets, can be relied upon.

For instance, the software can use a transformation matrix to move the foot to make its Brannock Axis coincide with the X Axis of the coordinate system. The origin can also be centered on the heel region. To identify the Brannock axis, 2 points are used: the medial extremum of the heel region and the medial extremum of the ball region. To find those points and the transformation matrix, the following algorithm can be used. "Vertices" can be 3D points defining triangles of the 3D model. In this algorithm, only the vertices 25 mm from the XY plane are used. (Z<25).

1. Calculate the approximate length of the pre-aligned foot by using the X coordinate of the Vertices: Length=Maximum X−Minimum X.
2. Define the heel and the ball region as follow:
   a. Heel Region: Minimum X<X<Minimum X+0.25*FootLength.
   b. Ball Region: Minimum X+0.65*FootLength<X<Maximum X.
3. Create a plane A parallel to the XZ plane that goes through the Minimum X vertex.
4. For each vertex in the model, create a plane B parallel to the Z Axis that go through the minimum X vertex and the current vertex.
   a. Calculate the angle W between plane B and Plane A.
   b. Find the vertex V that minimise (right foot) or maximise (left foot) the angle W.
5. Repeat Step 4 by starting with the new vertex V instead of minimum X vertex and find a new vertex V. It stops repeating when it finds a vertex V situated in the ball region.
6. The Brannock axis is the 2 lasts vertex V found in step 5.
7. Calculate the rotation matrix that will bring the Brannock Axis parallel to the X Axis and rotate the model.
8. Find the new minimum X vertex.
9. Calculate the translation vector to bring the minimum X Vertex on the origin and translate the model.
10. The foot is now aligned on the Brannock axis and centered on the heel. The transformation matrix is the combination of the rotation matrix and the translation vector.

Once the foot is aligned on its Brannock Axis, a set of predefined measurements can be calculated for applications such as orthotics and custom shoes.

Figure 4:
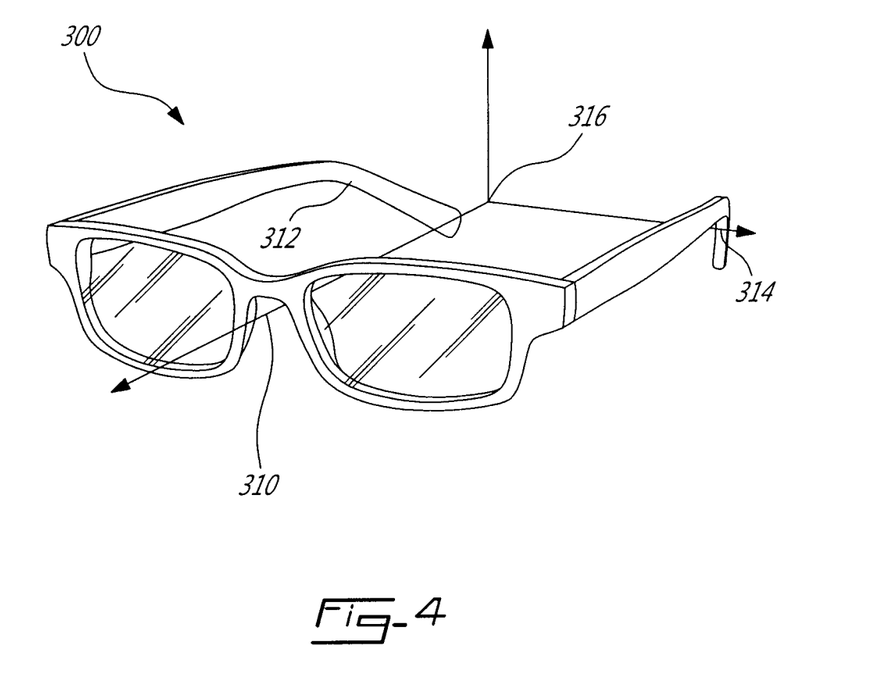
FIG. 4 is an oblique view showing a scanning module for a human head.

Referring now to FIG. 4, a second embodiment of a method to form a virtual model of a subject will now be described. In this second embodiment, the subject is a human head type. For instance, scanning the evolution of a baby's head can be very helpful in the context of a treatment for plagiocephaly correction. For this type of subject, an example of a scanning module can be in the form of a pair of glasses 300. In fact, although the head of a baby is subject to move much more than a adult foot resting on a planar surface is, using a scanning module in the form of a pair of glasses 300 allows the scanning module to nonetheless immobilize itself relative to the baby head (i.e. move collectively with the baby's head). More particularly, the scanning module can pre-align the head according to 3 specific feature locations: 1) the top of the nose (between the eyes), using a nose top abutment; 2) and 3) the top of left and right ears at the region where the ear connects to the head, using corresponding left and right ear abutments 312, 314.

Similarly to the foot subject type discussed above, the common coordinate system can thus be established in relation with the scanning module for all depth images to be correctly registered with one another into the 3D model of the head.

Using subject reference data, the type of model can become known to the software which can automatically clean-up noise, correct triangulation errors, fill undesirable holes in the model shell, and finalize the model for it to become "watertight" and ready to be sent to a CNC machine or CAD software for instance.

To compare the evolution of the head, the 3 specific abutment points of the scanning module can be used to form a virtual a reference plane which forms a roughly circular intersection with the model all around. A center point can be calculated from the roughly circular intersection and the evolving models of the head which can be taken every month during treatment for instance, can all be centered on their center point to be compared from one another. This can be done by positioning the origin of the model at the center point. If using Cartesian coordinates, the X axis can face the front (nose), the Y axis can face the side (ear), and the Z axis can point upwardly to the top of the head, for instance.

In this context, since the head can already be considered pre-aligned on its main alignment features, given the presence of the three subject-receiving abutments, detection may not be required and a more simple algorithm can be used :

1. Calculate a curve defined by the intersection of the XY plane and the surface of the 3D model.
2. Find the center of mass of this curve.
3. Find the translation vector necessary to bring this center of mass to the Origin.
4. Translate the head.
5. The head is now centered on its alignment features.

Measurements curves and statistics on the head geometry can now be calculated as they will be comparable from scan to scan, even if the head is growing.

If scanning targets are used on the scanning module, the scanning targets can be recorded in a file unique to a specific scanning module serial number. This virtual module model will be loaded as module reference data to be used in registering the different depth images of the head in the common reference system.

It can be understood from the above that since the glasses scanning module already fixes the relative immobilization of the head at three points, the complete orientation of the axes can be pre-set relative to the scanning module.

Figure 5:
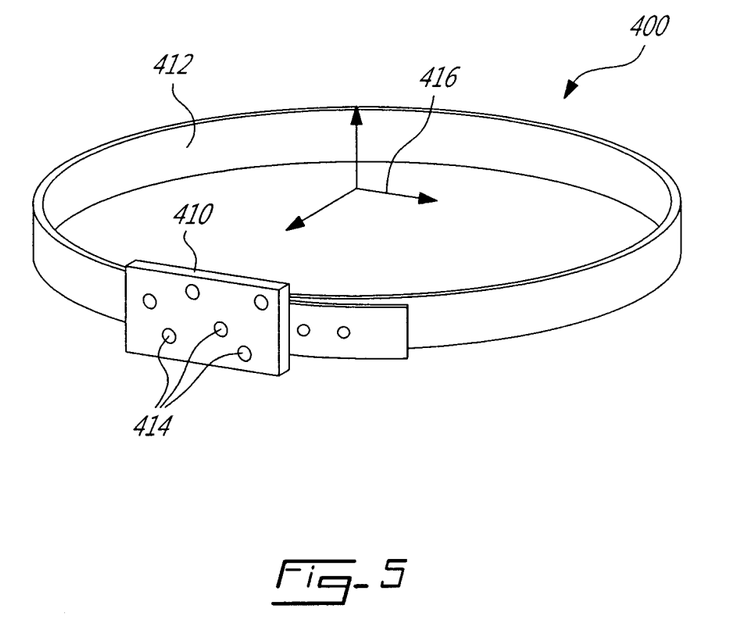
FIG. 5 is an oblique view showing a scanning module for a human torso.

Referring now to FIG. 5, a third specific embodiment of a method to form a virtual model of a subject will now be described. In this third embodiment, the subject is a torso. In this embodiment, the scanning module is provided in the form of a belt 400, and more specifically in the form of a belt buckle 410 which is immobilized at a given location between the person's bellybutton and groin area by way of the belt strap 412 being wrapped around the person's waist. In this specific example, the scanning module reference data is related to the unique pattern of a plurality of scanning targets 414 positioned on the outer face of the buckle, which fixes a common reference system 416 relative to the buckle. Alternate embodiments can use the buckle's known geometry as the basis of the common reference system, without scanning targets, for instance. If Cartesian coordinates are used, the origin can be located at the buckle, the X axis can point forward, the Z axis can point upward, and the Y axis can point toward the left of the subject, for instance.

The subject type can be predefined or inputted as being a torso prior to scanning. Once the scan is completed, the 3D images can be registered into a rough 3D model potentially having holes and noise. However, knowing the torso model type and its general alignment relative the buckle, the software can automatically fill the holes and finalize the model for it to become watertight, clean, free of triangulation errors, and ready to be sent to a CNC machine or other CAD software for instance.

If alignment of the virtual image needs to be done with a greater degree of precision than what can be achieved by the precision obtainable in the position of the buckle, additional precision can be obtained by using additional scanning targets on key physiological locations on the torso prior to scanning, for instance. Such additional scanning targets can be affixed on the sternum, coccyx, and $7^{th}$ cervical vertebra to name one possible example.

An example algorithm for the alignment of a torso on the middle axis can use a transformation matrix to move the torso so that its middle Axis coincides with the Z Axis of the coordinate system and to center the origin on this axis. To identify the middle axis, 2 points can be used: the center of the highest horizontal circumference curve and the center of the lowest horizontal circumference curve. To find those points and the transformation matrix, the following algorithm can be used:

1. Find the highest and lowest point in Z on the model and calculate the highest and lowest circumference at ZMax−20 mm and ZMin+20 mm.

2. Find the center of the ZMax and ZMin curves in the XY Plane.

3. Calculate the middle axis Vector from ZMax curve center point and ZMin curve center point.

4. Calculate the rotation matrix that will bring the middle axis parallel to the Z Axis and rotate the model.

5. Calculate the translation vector to bring the minimum ZMin center vertex on the origin and translate the model.

6. The torso is now aligned on the middle axis and centered on ZMin Center vertex. The transformation matrix is the combination of the rotation matrix and the translation vector.

Once the torso is aligned on its Middle axis, a complete set of measurements can be calculated to help with the design of a brace or another kind of equipment, for instance.

In an embodiment where positioning features are affixed on the sternum, the coccyx and the 7th cervical vertebra as key anatomical locations, it is possible to align the torso according to theses points as well. This kind of alignment can be used for comparison with another torso, healthy or diseased, in order to calculate statistics and help the diagnostic. It can also be used to compare with a virtual model of a sport equipment or garment to evaluate the shape and size.

The examples described above and illustrated are intended to be exemplary only. The scope is indicated by the appended claims.

What is claimed is:

1. A method of forming a virtual model of a subject using at least a hand-held scanner and a scanning module adapted specifically to receive the subject in a predetermined position and orientation, the method comprising:
   providing module reference data concerning the scanning module;
   providing subject reference data;
   immobilizing the subject in the predetermined position and orientation relative to the scanning module;
   obtaining a plurality of depth images of the immobilized subject and module, the depth images being from corresponding different points of view relative to a ground reference;
   determining a position and an orientation of the scanning module in each one of the depth images using the module reference data; and
   forming the virtual model of the subject including registering the plurality of depth images using the determined position and orientation of the scanning module and at least one of completing and correcting the alignment of the registered depth images using the subject reference data;
   wherein the subject is a human head and the scanning module includes a nose abutment, a left ear abutment, and a right ear abutment, further comprising: determining a position and orientation of the head based on the determined position and orientation of the scanning module.

2. The method of claim 1 wherein the subject reference data includes a rough expected shape, position and orientation of the subject relative to the scanning module.

3. The method of claim 1 further comprising positioning at least one scanning target at a corresponding physiological feature location on the subject prior to said obtaining the plurality of depth images, wherein the subject reference data includes said physiological feature location of said at least one scanning target.

4. The method of claim 1 wherein said obtaining is done using a hand held scanner.

5. The method of claim 4 wherein said hand-held scanner is an active surface scanner including at least an emitter and a detector, the model is a shell model, and the subject reference data includes at least one expected opening position and size in the shell model relative to a position and orientation of the scanning module in the common reference system.

6. The method of claim 1 wherein the scanning module has scanning targets on a surface thereof, and said module reference data includes position information of the scanning targets on the scanning module, wherein said determining a position and an orientation of the scanning module in the depth image includes identifying scanning targets in the depth image and associating the identified scanning targets to said scanning targets in the module reference data.

7. The method of claim 1 wherein the module reference data includes configuration information of the shape of the scanning module, wherein said determining a position and an orientation of the scanning module in the depth image includes associating a shape in the depth image to the configuration information in the module reference data.

8. The method of claim 1 wherein the scanning module includes an electromagnetic field emitter emitting an electromagnetic field in the vicinity of the scanning module, the hand-held scanner includes an electromagnetic field detector, and said module reference data includes configuration information of the electromagnetic field, wherein said determining a position and an orientation of the scanning module in the depth image includes comparing an electromagnetic signal detected by the electromagnetic field detector to the configuration information in the module reference data.

9. The method of claim 1 further comprising obtaining a virtual model of an other subject of the same type, and comparing the virtual model of the subject to the virtual model of the other subject of the same type.

10. The method of claim 1 further comprising obtaining a virtual model of a garment to be worn on the subject, and comparing the virtual model of the subject to the virtual model of the garment.

11. The method of claim 1 further comprising using the virtual model in the designing of an object to be worn on the subject.

12. A method of forming a virtual model of a subject using at least a hand-held scanner and a scanning module adapted specifically to receive the subject in a predetermined position and orientation, the method comprising:
    providing module reference data concerning the scanning module;
    providing subject reference data;
    immobilizing the subject in the predetermined position and orientation relative to the scanning module;
    obtaining a plurality of depth images of the immobilized subject and module, the depth images being from corresponding different points of view relative to a ground reference;
    determining a position and an orientation of the scanning module in each one of the depth images using the module reference data; and
    forming the virtual model of the subject including registering the plurality of depth images using the determined position and orientation of the scanning module and at least one of completing and correcting the alignment of the registered depth images using the subject reference data;
    wherein the subject is a human torso and the scanning module is securable around the waist thereof.

13. The method of claim 12 further comprising positioning at least one scanning target at a corresponding physiological feature location on the torso prior to said obtaining the plurality of depth images, and detecting the position of the at least one scanning target in the virtual model; further comprising determining an orientation of the torso using the detected position of the at least one scanning target.

14. A system for forming a virtual model of a subject, the system comprising:
    a scanning module having at least one subject-receiving abutment associated to a reference plane;
    a memory for storing module reference data of the scanning module, said module reference data including a location of the reference plane;
    a software application capable of accessing the module reference data, receiving a plurality of depth images, from a plurality of points of view, of the scanning module and of the subject immobilized relative to the scanning module, and operable to determine a position and an orientation of the reference plane in each of the depth images using the module reference data; and
    a software application operable to register the plurality of depth images using the determined position and orientation of the reference plane and to produce the virtual image of the subject based thereon;
    wherein the subject is a human head, the scanning module is in the form of a pair of glasses, and the at least one subject-receiving abutment includes a nose abutment, a left ear abutment, and a right ear abutment.

15. The system of claim 14 wherein the scanning module has scanning targets on a surface thereof, and said module reference data includes position information of the scanning targets on the scanning module.

16. The system of claim 14 wherein the scanning module includes an electromagnetic field emitter emitting an electromagnetic field in the vicinity of the scanning module, the hand-held scanner includes an electromagnetic field detector, and said module reference data includes configuration information of the electromagnetic field.

17. The system of claim 14 wherein the module reference data includes configuration information of the shape of the scanning module.

18. The system of claim 14 wherein the subject includes at least one scanning target on a physiological feature thereof, and the subject reference data includes information of the physiological feature having the scanning target.

19. The system of claim 14 further comprising a hand-held scanner to obtain the plurality of depth images, the hand-held scanner being an active surface scanner including at least an emitter and a detector, and the model is a shell model.

20. The system of claim 14 further comprising:
    a memory for storing subject reference data; and
    a software for determining a position and an orientation of the subject in each depth image using the subject reference data.

21. A system for forming a virtual model of a subject, the system comprising:
    a scanning module having at least one subject-receiving abutment associated to a reference plane;
    a memory for storing module reference data of the scanning module, said module reference data including a location of the reference plane;
    a software application capable of accessing the module reference data, receiving a plurality of depth images, from a plurality of points of view, of the scanning module and of the subject immobilized relative to the scanning module, and operable to determine a position and an orientation of the reference plane in each of the depth images using the module reference data; and
    a software application operable to register the plurality of depth images using the determined position and orientation of the reference plane and to produce the virtual image of the subject based thereon;

wherein the subject is a human torso, the scanning module is in the form of a belt, and the at least one subject-receiving abutment includes a strap attachable around the waist of the torso.

* * * * *